(12) United States Patent
Petersen et al.

(10) Patent No.: US 6,660,873 B2
(45) Date of Patent: Dec. 9, 2003

(54) METHOD FOR THE PREPARATION OF CITALOPRAM

(75) Inventors: Hans Petersen, Vanløse (DK); Robert Dancer, Frederiksberg C (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/291,174

(22) Filed: Nov. 8, 2002

(65) Prior Publication Data

US 2003/0134895 A1 Jul. 17, 2003

Related U.S. Application Data

(63) Continuation of application No. PCT/DK01/00333, filed on May 10, 2001.

(30) Foreign Application Priority Data

May 12, 2000 (DK) .................. PA 2000 00783

(51) Int. Cl.[7] ............................................ C07D 307/78
(52) U.S. Cl. ................................................ 549/467
(58) Field of Search ................................. 549/469, 467

(56) References Cited

U.S. PATENT DOCUMENTS

| | | | |
|---|---|---|---|
| 3,467,675 A | 9/1969 | Petersen et al. | 260/346.2 |
| 4,136,193 A | 1/1979 | Bogeso et al. | 424/285 |
| 4,650,884 A | 3/1987 | Bogeso | 549/467 |
| 4,943,590 A | 7/1990 | Boegesoe et al. | 514/469 |
| 5,296,507 A | 3/1994 | Tanaka et al. | 514/465 |
| 6,020,501 A | 2/2000 | Massonne et al. | 549/307 |
| 6,028,204 A | 2/2000 | Massonne et al. | 549/307 |
| 6,229,026 B1 | 5/2001 | Petersen | 549/467 |
| 6,258,842 B1 | 7/2001 | Petersen et al. | 514/469 |
| 6,291,689 B1 | 9/2001 | Petersen et al. | 549/467 |
| 6,310,222 B1 | 10/2001 | Ikemoto et al. | 549/467 |
| 6,365,747 B1 | 4/2002 | Dall'Asta et al. | 548/146 |
| 6,392,060 B2 | 5/2002 | Petersen et al. | 549/307 |
| 6,403,813 B1 | 6/2002 | Petersen et al. | 549/305 |
| 6,407,267 B1 | 6/2002 | Rock et al. | 549/467 |
| 6,420,574 B2 | 7/2002 | Petersen et al. | 549/467 |
| 6,426,422 B1 | 7/2002 | Petersen et al. | 549/467 |
| 6,433,196 B1 | 8/2002 | Ikemoto et al. | 549/469 |
| 6,441,201 B1 | 8/2002 | Weber | 549/468 |
| 6,455,710 B1 | 9/2002 | Villa et al. | 549/462 |
| 6,458,973 B1 | 10/2002 | Dall'Asta et al. | 549/305 |

(List continued on next page.)

FOREIGN PATENT DOCUMENTS

| | | | |
|---|---|---|---|
| WO | WO 98/19511 | 5/1998 | |
| WO | 98/19512 | 5/1998 | |
| WO | 98/19513 | 5/1998 | |
| WO | 99/30548 | 6/1999 | |
| WO | 00/11926 | 3/2000 | |
| WO | 00/12044 | 3/2000 | |
| WO | 00/13648 | 3/2000 | |
| WO | 00/23431 | 4/2000 | C07D/307/87 |
| WO | 00/39112 | 7/2000 | C07D/307/87 |
| WO | 00/44738 | 8/2000 | C07D/307/88 |
| WO | 01/02383 | 1/2001 | C07D/307/87 |
| WO | 01/45483 | 6/2001 | |
| WO | 01/47877 | 7/2001 | |
| WO | 01/47909 | 7/2001 | C07D/307/87 |
| WO | 01/49672 | 7/2001 | C07D/307/87 |
| WO | 01/51477 | 7/2001 | C07D/307/87 |
| WO | 01/51478 | 7/2001 | C07D/307/87 |
| WO | 01/62754 | 8/2001 | C07D/307/87 |
| WO | 01/66536 | 9/2001 | C07D/307/87 |
| WO | 01/68627 | 9/2001 | C07D/307/87 |
| WO | 01/68628 | 9/2001 | C07D/307/87 |
| WO | 01/68629 | 9/2001 | C07D/307/87 |
| WO | 01/68630 | 9/2001 | C07D/307/87 |
| WO | 01/68631 | 9/2001 | C07D/307/87 |
| WO | 01/68632 | 9/2001 | C07D/307/87 |
| WO | 01/85712 | 11/2001 | C07D/307/87 |
| WO | 02/04435 | 1/2002 | C07D/307/87 |

OTHER PUBLICATIONS

E.A.L. Biessen et al. "Partial Purification of the 5–Hydroxytryptophan–Reuptake System from Human Blood Platelets Using a Citalopram–Derived Affinity Resin", *Biochemistry* 1990, 29, 3349–3354.

U.S. Patent Application Ser. No. 10/183,958, filed Jun. 25, 2002.

U.S. Patent Application Ser. No. 10/191,808, filed Jul. 8, 2002.

U.S. Patent Application Ser. No. 10/232,994, filed Aug. 29, 2002.

U.S. Patent Application Ser. No. 10/233,132, filed Aug. 30, 2002.

U.S. Patent Application Ser. No. 10/237,145, filed Sep. 5, 2002.

U.S. Patent Application Ser. No. 10/238,907, filed Sep. 6, 2002.

U.S. Patent Application Ser. No. 10/228,388, filed Aug. 23, 2002.

U.S. Patent Application Ser. No. 10/238,843, filed Sep. 9, 2002.

U.S. Patent Application Ser. No. 10/245,824, filed Sep. 12, 2002.

U.S. Patent Application Ser. No. 10/242,804, filed Sep. 10, 2002.

U.S. Patent Application Ser. No. 10/291,174, filed Nov. 8, 2002.

Levy, L.F., "4–Aminophthalide and Some Derivatives", *J. Chem Soc*. pp. 867–870 (1931).

Tirouflet, Jean, "Phtalide Substitués en 5", *Bull. Soc. Sci. de Bretagne* 26:35–43 (1951).

(List continued on next page.)

*Primary Examiner*—Amelia Owens
(74) *Attorney, Agent, or Firm*—Darby & Darby

(57) ABSTRACT

A method for the preparation of citalopram comprising reaction of a compound of formula 5-aminomethyl-1-(3-dimethylamino-propyl)-1-(4-fluoro-phenyl)-1,3-dihydro-isobenzofuran with an oxidising agent to prepare citalopram.

21 Claims, No Drawings

U.S. PATENT DOCUMENTS

| | | | |
|---|---|---|---|
| 2002/0004604 A1 | 1/2002 | Petersen et al. | 549/462 |
| 2002/0026062 A1 | 2/2002 | Petersen et al. | 549/467 |
| 2002/0035277 A1 | 3/2002 | Rock et al. | 549/467 |
| 2002/0040153 A1 | 4/2002 | Petersen | 549/467 |
| 2002/0061925 A1 | 5/2002 | Petersen et al. | 514/469 |
| 2002/0077353 A1 | 6/2002 | Petersen et al. | 514/469 |
| 2002/0087012 A1 | 7/2002 | Castellin et al. | 549/467 |
| 2002/0128497 A1 | 9/2002 | Bolzonella et al. | 549/467 |
| 2002/0165403 A1 | 11/2002 | Petersen et al. | 549/467 |
| 2002/0198391 A1 | 12/2002 | Petersen et al. | 549/307 |

OTHER PUBLICATIONS

Forney, LeRoy S.., "Reaction of Terephthalic Acid with Formaldehyde in Sulfur Trioxide Media," *J. Org. Chem.* 35:1695–1696 (1970).

Dordor, Isabelle M. et al., "Reaction of Oxazolines with Phosphorus Oxychloride," *Tetrahedron Letters* 24:1437–1440 (1983).

Barton, Sir Derek et al., *Comprehensive Organic Chemistry. The Synthesis and Reactions of Organic Compounds*, vol. 2, pp. 1024–1025.

Bigler, Allan J. et al., "Quantitative structure–activity relationships in a series of selective 5–HT uptake inhibitors," *Eur. J. Med. Chem.* (1977) 12, 3: 289–295.

METHOD FOR THE PREPARATION OF CITALOPRAM

This application is a continuation of International application no. PCT/DK01/00333, filed May 10, 2001. The prior application is hereby incorporated by reference in its entirety.

The present invention relates to a method for the preparation of the well-known antidepressant drug citalopram, 1-[3-(dimethylamino)propyl]-1-(4-fluorophenyl)-1,3-dihydro-5-isobenzofuran-carbonitrile.

BACKGROUND OF THE INVENTION

Citalopram is a well-known antidepressant drug that has now been on the market for some years and has the following structure:

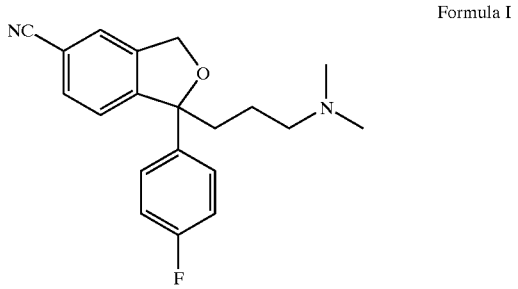

Formula I

It is a selective, centrally acting serotonin (5-hydroxytryptamine; 5-HT) reuptake inhibitor, accordingly having antidepressant activities. The antidepressant activity of the compound has been reported in several publications, eg. J. Hyttel *Prog. Neuro-Psychopharmacol. & Biol. Psychiat.* 1982, 6, 277–295 and A. Gravem, *Acta Psychiatr. Scand.* 1987, 75, 478–486. The compound has further been disclosed to show effects in the treatment of dementia and cerebrovascular disorders, EP-A 474580.

Citalopram was first disclosed in DE 2,657,013, corresponding to U.S. Pat. No. 4,136,193. This patent publication describes the preparation of citalopram by one method and outlines a further method, which may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

According to the method, which is only outlined in general terms, citalopram may be obtained by ring closure of the compound:

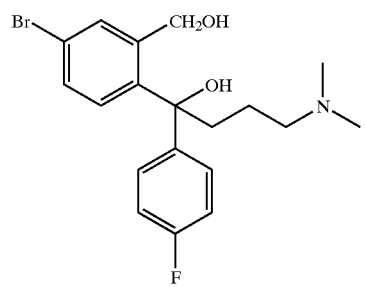

Formula II in the presence of a dehydrating agent and subsequent exchange of the 5-bromo group with cuprous cyanide. The starting material of Formula II is obtained from 5-bromophthalide by two successive Grignard reactions, i.e. with 4-fluorophenyl magnesium chloride and N,N-dimethylaminopropyl magnesium chloride, respectively.

A new and surprising method and an intermediate for the preparation of citalopram were described in U.S. Pat. No. 4,650,884, according to which an intermediate of the formula

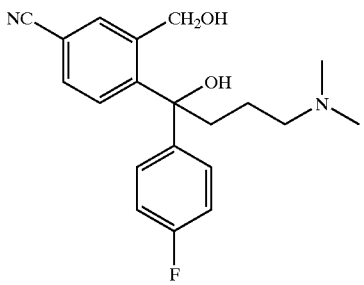

Formula III is subjected to a ring closure reaction by dehydration with strong sulfuric acid in order to obtain citalopram. The intermediate of Formula III was prepared from 5-cyanophthalide by two successive Grignard reactions, i.e. with 4-fluorophenyl magnesium halogenide and N,N-dimethylaminopropyl magnesium halogenide, respectively.

Further processes are disclosed in International patent applications nos. WO 98/019511, WO 98/019512 and WO 98/019513. WO 98/019512 and WO 98/019513 relate to methods wherein a 5-amino-, 5-carboxy- or 5-(sec. aminocarbonyl)phthalide is subjected to two successive Grignard reactions, ring closure and conversion of the resulting 1,3-dihydroisobenzofuran derivative to the corresponding 5-cyano compound, i.e. citalopram. International patent application no. WO 98/019511 discloses a process for the manufacture of citalopram wherein a (4-substituted-2-hydroxymethylphenyl-(4-fluorophenyl)methanol compound is subjected to ring closure and the resulting 5-substituted 1-(4-fluorophenyl)-1,3-dihydroisobenzofuran converted to the corresponding 5-cyano derivative which is alkylated with a (3-dimethylamino)propylhalogenide in order to obtain citalopram.

Finally, methods for preparing the individual enantiomers of citalopram are disclosed in U.S. Pat. No. 4,943,590 from which it also appears that the ring closure of the intermediate of Formula III may be carried out via a labile ester with a base.

It has now, surprisingly, been found that citalopram may be manufactured by a novel favourable and safe procedure using convenient starting materials.

SUMMARY OF THE INVENTION

Accordingly, the present invention relates to a novel method for the preparation of citalopram comprising reaction of a compound of Formula IV

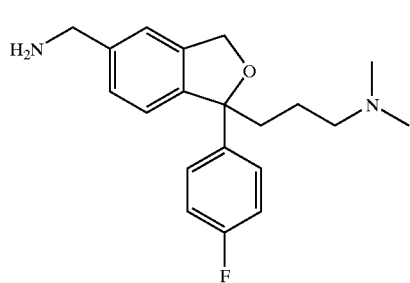

Formula IV with an appropriate oxidising agent such as copper(I) and $O_2$; or $NiSO_4$ and $K_2S_2O_8$ to afford citalopram

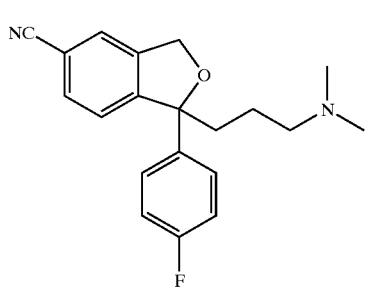

Formula I which is isolated as the base or a pharmaceutically acceptable salt thereof.

In another aspect, the invention relates to methods for preparing the intermediates of Formula IV.

In yet another aspect, the present invention relates to an antidepressant pharmaceutical composition comprising citalopram as the base or any convenient salt thereof manufactured by the process of the invention.

Furthermore, according to the invention, the compounds of Formula IV may be prepared by different methods.

One of these methods includes the following steps:

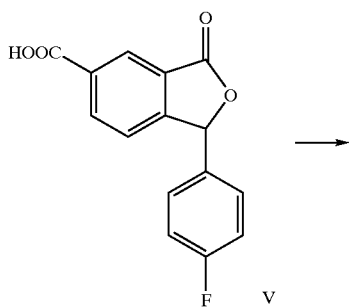

V

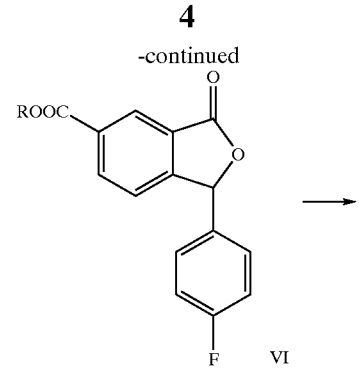

VI

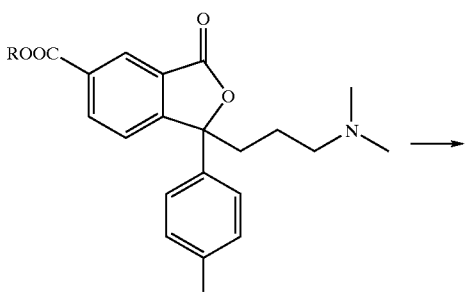

VII

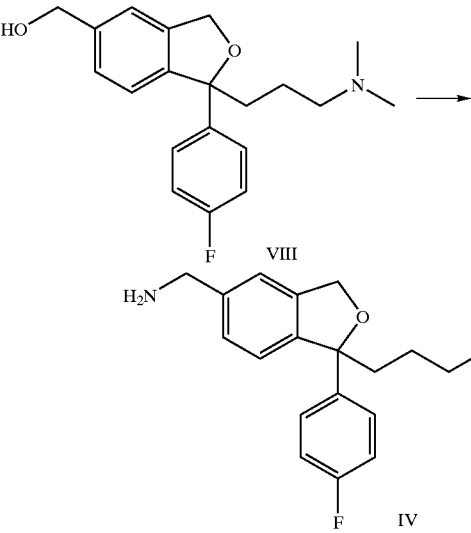

VIII

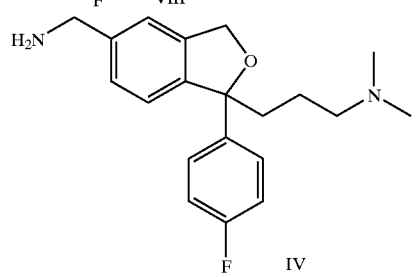

IV 6-carboxy-3-(4-fluorophenyl)phthalide is reacted with an alcohol, R-OH, wherein R is preferably lower alkyl, most preferably Me, in the presence of a dehydrating agent, preferably $SOCl_2$.

The resulting compound of Formula VI is alkylated with

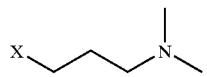

wherein X is a leaving group in the presence of a suitable base. X is preferably halogen or sulphonate.

Optionally, the alkylating reaction is a stepwise alkylation. In this case, the resulting compound of Formula VI is alkylated with a compound having the formula

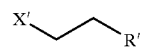

wherein X' is a suitable leaving group and R' is —$CH_2$—O-Pg, —$CH_2$-$NPg_1Pg_2$, —CO—$N(CH_3)_2$, —$CH(OR^1)$ (OR$^2$), —C(OR$^4$)(OR$^5$)(OR$^6$) or —COOR$^3$; wherein Pg is a protection group for an alcohol group, Pg$_1$ and Pg$_2$ are protection groups for an amino group, R$^1$ and R$^2$ are alkyl groups or R$^1$ and R$^2$ together form a chain of 2 to 4 carbon atoms and R$^3$, R$^4$, R$^5$ and R$^6$ are alkyl, alkenyl, alkynyl, aryl or aralkyl;

to form a compound of Formula XVIII

Formula XVIII

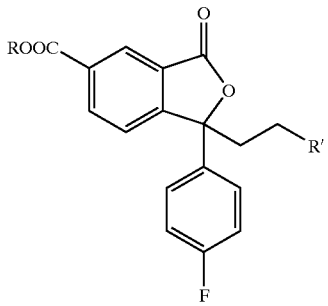

wherein R' is as defined above; followed by conversion of the group R' to a dimethylaminomethyl group.

The resulting compound of Formula VII is reacted with a reducing agent such as LiAlH$_4$, Red-Al, AlH$_3$ or activated forms of NaBH$_4$, e.g. NaBH$_4$, Me$_2$SO$_4$; NaBH$_4$, I$_2$; NaBH$_4$, BF$_3$.Et$_2$O; or B$_2$H$_6$; followed by treatment with acid or another dehydrating agent to perform ring closure to form the compound of Formula VIII.

The alcohol of Formula VIII is conveniently activated by tosylchloride or mesylchloride to form the corresponding substituted sulphonate; or the alcohol is converted into the corresponding benzylic halide. This conversion is preferably carried out with SOBr$_2$ or SOCl$_2$.

The corresponding sulphonate or halide is either converted directly to the compound of Formula IV by reaction with liquid ammonia;

or by a reaction with a metal salt of phthalimide, preferably potassium phthalamide followed by treatment with NH$_2$NH$_2$ or by treatment with an amine in an alcohol, i.e. R$^8$NH$_2$/R$^9$—OH, wherein R$^8$ and R$^9$ are lower alkyl, preferably methyl or ethyl, e.g. methylamine in ethanol;

or by a reaction with metal azide, MN$_3$, M preferably being Na or K; followed by treatment with a reducing agent such as Pd/C and H$_2$ or a hydrate source such as LiAlH$_4$ or NaBH$_4$ or an activated form of it.

Another method for preparing the compound of Formula IV includes the following steps:

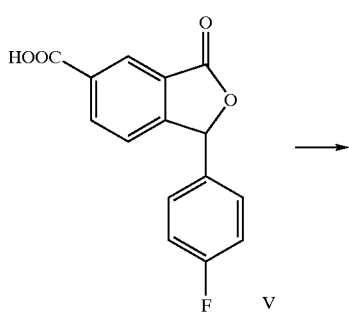

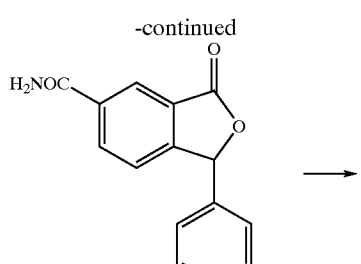

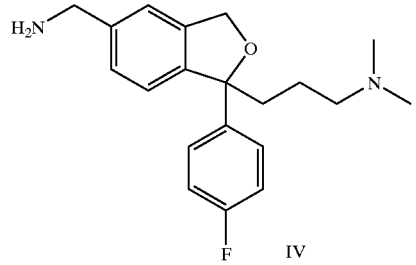

6-carboxy-3-(4-fluorophenyl)phthalide is conveniently reacted with a dehydrating agent such as thionylchloride, followed by aminolysis of the resulting activated acid derivative.

The resulting compound of Formula IX is alkylated with

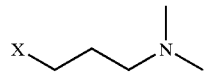

wherein X is a leaving group in the presence of a suitable base. X is preferably halogen or sulphonate.

Optionally, the alkylating reaction is a stepwise alkylation analogous to the stepwise alkylation described above.

The resulting compound of Formula X is reacted with a reducing agent such as LiAlH$_4$, Red-Al, AlH$_3$ or activated forms of NaBH$_4$, e.g. NaBH$_4$, Me$_2$SO$_4$; NaBH$_4$, I$_2$; NaBH$_4$, BF$_3$.Et$_2$O; or B$_2$H$_6$; followed by treatment with acid or another dehydrating agent to perform ring closure to form the compound of Formula IV.

According to a third method for preparing the compound of Formula IV, the corresponding 6-cyano substituted derivative of 6-carboxy-3-(4-fluorophenyl)phthalide is prepared.

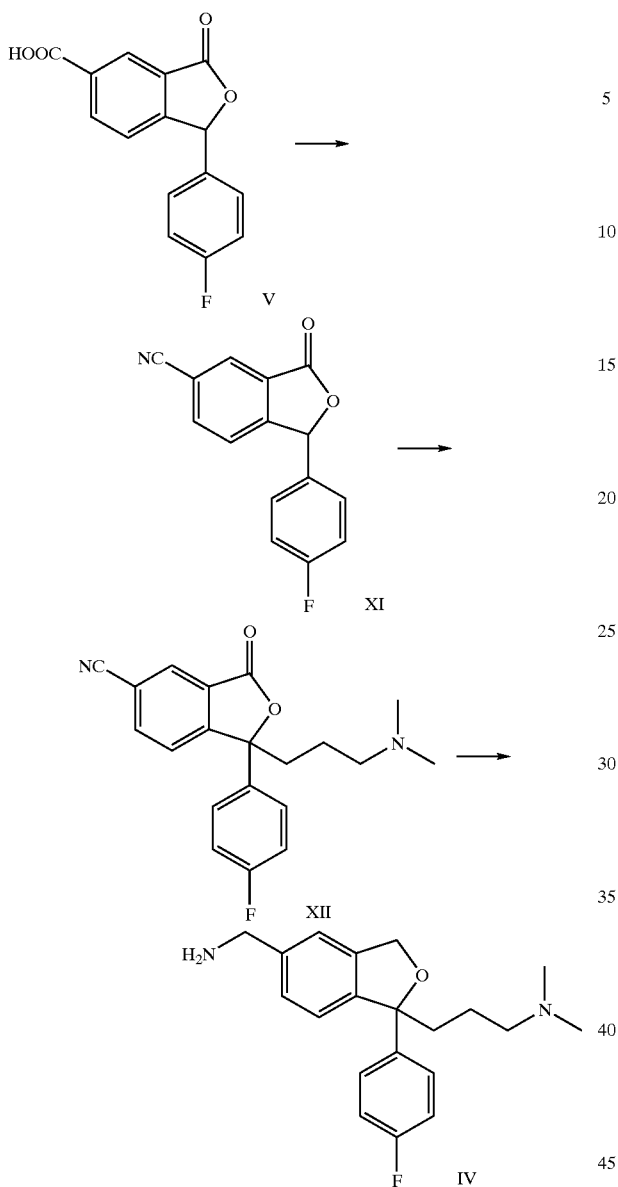

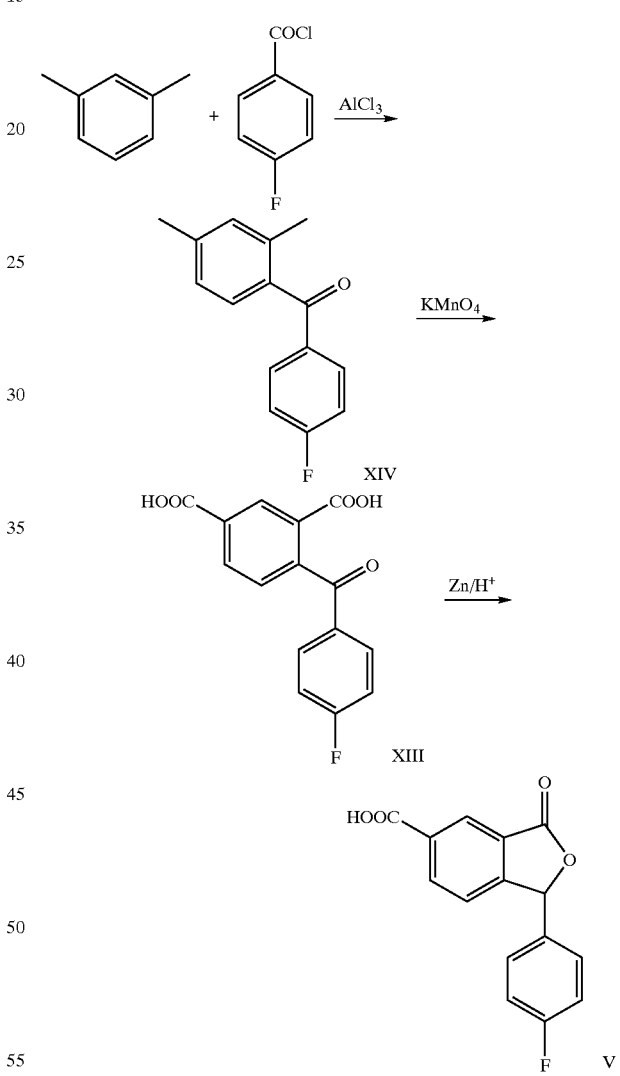

forms of NaBH$_4$, e.g. NaBH$_4$, Me$_2$SO$_4$; NaBH$_4$, I$_2$; NaBH$_4$, BF$_3$.Et$_2$O; or B$_2$H$_6$; followed by treatment with acid to perform ring closure to form the compound of Formula IV.

Other reaction conditions, solvents, etc. for the reactions described above are conventional conditions for such reactions and may easily be determined by a person skilled in the art.

In another aspect, the present invention provides the novel intermediate of Formula V.

In a further aspect, the invention relates to methods for preparing the intermediate of Formula V.

One stepwise process for preparing the intermediate of Formula V is illustrated below:

The carboxy derivative is either reacted with SOCl$_2$ followed by treatment with ammonia and finally a dehydrating agent such as SOCl$_2$ to prepare the cyano derivative of Formula XI; or reacted with an alcohol R—OH in the presence of acid followed by treatment with ammonia and finally reacted with SOCl$_2$; or reacted in a one-pot process such as with SO$_2$(NH$_2$)$_2$, SOCl$_2$ and sulfolane, or with tert-butylamine, a dehydrating agent such as POCl$_3$ and a suitable solvent, such as toluene.

The resulting compound of Formula XI is alkylated with

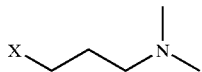

wherein X is a leaving group in the presence of a suitable base. X is preferably halogen or sulphonate.

Optionally, the alkylating reaction is a stepwise alkylation analogous to the stepwise alkylation described above.

The resulting compound of Formula XII is reacted with a reducing agent such as LiAlH$_4$, Red-Al, AlH$_3$ or activated m-xylene and p-fluorobenzoyl chloride, which are commercially available compounds are reacted in the presence of AlCl$_3$ to afford the compound of Formula XIV. This compound is oxidised with permanganate, preferably KMnO$_4$ or NaMnO$_4$, giving the resulting compound of Formula XIII, which is finally reacted conveniently with Zn in acid, preferably acetic acid.

Alternatively, the compound of Formula IV is prepared from the compound of Formula XIII by the following stepwise process:

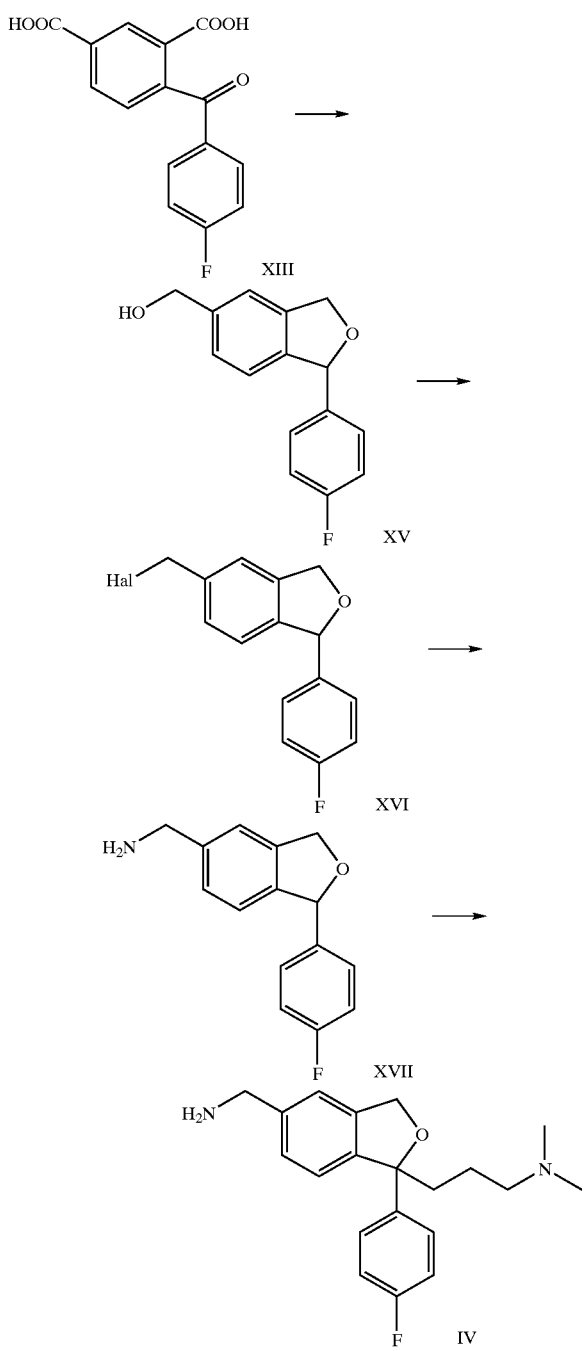

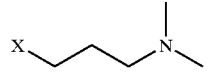

The compound of Formula XIII is reacted with a reducing agent such as LiAlH$_4$, Red-Al, AlH$_3$ or activated forms of NaBH$_4$, e.g. NaBH$_4$, Me$_2$SO$_4$; NaBH$_4$, I$_2$; NaBH$_4$, BF$_3$.Et$_2$O; or B$_2$H$_6$; followed by treatment with acid to perform ring closure to form the compound of Formula XV.

The alcohol of Formula XV is conveniently activated by tosylchloride or mesylchloride to form the corresponding substituted sulphonate; or the alcohol is converted into the corresponding benzylic halide. This conversion is preferably carried out with SOBr$_2$ or SOCl$_2$.

The corresponding sulphonate or halide is either converted directly to the compound of Formula XVII by reaction with liquid ammonia;

or by a reaction with a metal salt of phthalimide, preferably potassium phthalamide, followed by treatment with NH$_2$NH$_2$ or by treatment with an amine in an alcohol, i.e. R$^8$NH$_2$/R$^9$—OH, wherein R$^8$ and R$^9$ are lower alkyl, preferably methyl or ethyl, e.g. methylamine in ethanol; or by a reaction with metal azide MN$_3$, M preferably being Na or K; followed by treatment with a reducing agent such as Pd/C and H$_2$ or a hydride source such as LiAlH$_4$ or NaBH$_4$ or an activated form thereof.

The resulting compound of Formula XVII is alkylated with wherein X is a leaving group in the presence of a suitable base. X is preferably halogen or sulphonate.

Optionally, the alkylating reaction is a stepwise alkylation analogous to the stepwise alkylation described above.

Optionally the steps of the alkylation and the conversion to the cyano derivative are in opposite order so the conversion to the cyano derivative is performed before the alkylation.

Throughout the specification and claims, the terms lower alkyl or C$_{1-6}$ alkyl refer to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl.

Similarly, alkenyl and alkynyl, respectively, designate such groups having from two to six carbon atoms, including one double bond and triple bond respectively, such as ethenyl, propenyl, butenyl, ethynyl, propynyl, and butynyl.

The term aryl refers to a mono- or bicyclic carbocyclic aromatic group, such as phenyl and naphthyl, in particular phenyl.

The term aralkyl refers to aryl-alkyl, wherein aryl and alkyl are as defined above.

Halogen means chloro, bromo or iodo.

The compound of general Formula I may be used as the free base or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of the compounds may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvant or additive, colouring, aroma, preservative etc. may be used provided that they are compatible with the active ingredients.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

EXAMPLES

The invention is further illustrated by the following examples.

Example 1

5-Aminomethyl-1-(3-dimethylamino-propyl)-1-(4-fluoro-phenyl)-1,3-dihydro-isobenzofuran 1-(3-Dimethylamino-propyl)-1-(4-fluoro-phenyl)-3-oxo-1,3-dihydro-isobenzofuran-5-carbonitrile (5.4 g, 16.2 mmol) was dissolved in dry THF (5 mL) and diluted with dry ether (50 mL). This solution was added dropwise to a refluxing suspension of lithium aluminium hydride (2.5 g, 65 mmol) in dry ether (150 mL) over 10–15 minutes, after which the resulting suspension was heated at reflux for a further 4 h. The solution was allowed to cool to room temperature and was stirred at room temperature overnight. The reaction was quenched with a minimum of water, and the resulting solution/suspension was dried over anhydrous magnesium sulfate. The mixture was filtered, and the solid cake was washed with THF. The combined filtrates were evaporated to give an oil. The oil was dissolved in toluene (200 mL) and was stirred with an aqueous solution of sulfuric acid (10 ml, 70% v/v) for 3 h. The mixture was diluted with water, and the pH was adjusted to >9 by the addition of aqueous ammonia solution (25% w/v). The toluene was separated, and the aqueous phase was extracted with further toluene. The combined toluene extracts were dried over anhydrous magnesium sulfate, filtered and evaporated to give the title compound as a yellow oil (4.4 g, 84%). $^1$H NMR (CDCl$_3$): δ 1.25–1.40 (m, 1H), 1.40–1.55 (m, 1H), 2.11 (ddd, 1H), 2.13 (t, 3H), 2.15 (ddd, 1H), 2.21 (t, 2H), 3.85 (s, 2H), 5.11 (d, 1H), 5.14 (d, 1H), 6.96 (t, 2H), 7.15 (s, 1H), 7.21 (d, 1H), 7.22 (d, 1H), 7.45 (dd, 2H).

Example 2

Citalopram, HBr

A mixture of 5-aminomethyl-1-(3-dimethylamino-propyl)-1-(4-fluoro-phenyl)-1,3-dihydroisobenzofuran (10 g, 30 mmol) and 5 Å molecular sieves (24 g) in pyridine (150 mL) was stirred at 60° C. under an atmosphere of oxygen. Copper(I) chloride (1.8 g, 1.8 mmol) was added, and the mixture was stirred for 3 h. Further copper(I) chloride (1.8 g, 1.8 mmol) was added, and the mixture was stirred overnight. The mixture was poured onto ice, and the pH of the mixture was adjusted to >9 by the addition of aqueous ammonia solution (25% w/v). The solution was diluted with toluene and filtered. The organic phase was separated, and the aqueous was washed with further toluene. The combined organic extracts were washed with water, dried over anhydrous sodium sulfate and evaporated. The residue was treated with heptane and was evaporated to give an oil (11.1 g). This oil was dissolved in acetone and treated with aqueous hydrobromic acid (7 ml, 47% w/v). The solution was evaporated, and the residue was dissolved in iso-propanol (100 mL). The solution was stirred overnight. The resulting precipitate was filtered and dried to give the HBr salt of citalopram as a white powder (8.2 g, 66%). The filtrate was evaporated, and the oily residue was shaken with ether and allowed to stand overnight. Filtration of the solution gave further HBr salt of citalopram as a brown solid (1.7 g, 14%). $^1$H NMR (d$^6$-DMSO): δ 1.35–1.50 (m, 1H), 1.50–1.60 (m, 1H), 2.25 (t, 2H), 2.69 (s, 3H), 3.00–3.10 (m, 2H), 5.17 (d, 1H), 5.25 (d, 1H), 7.18 (t, 2H), 7.61 (dd, 2H), 7.77 (d, 1H), 7.82 (d, 1H), 7.83 (s, 1H), 9.27 (bs, 1H).

Example 3

1-(4-Fluoro-phenyl)-3-oxo-1,3-dihydro-isobenzofuran-5-carboxylic Acid Methyl Ester A stirred suspension of 1-(4-fluoro-phenyl)-3-oxo-1,3-dihydro-isobenzofuran-5-carboxylic acid (1 g, 3.7 mmol) in thionyl chloride (25 mL) was heated at reflux for 25 min, during which time the solid dissolved. The thionyl chloride was then evaporated, and the residue was dissolved in toluene, and again evaporated. The residue was stirred in methanol (25 mL) overnight, during which time a heavy precipitate formed. The solvent was evaporated, and the residue was partitioned between aqueous ammonia solution (25% w/v) and toluene. The organic phase was separated, dried over magnesium sulfate and evaporated to give the title compound as a white solid (0.97 g, 92%). $^1$H NMR (d$^6$-DMSO): δ 3.92 (s, 3H), 6.85 (s, 1H), 7.26 (t, 2H), 7.42 (dd, 2H), 7.61 (d, 1H), 8.31 (dd, 1H), 8.36 (s, 1H).

Example 4

1-(4-Fluoro-phenyl)-3-oxo-1,3-dihydro-isobenzofuran-5-carboxylic Acid Amide

A stirred suspension of 1-(4-fluoro-phenyl)-3-oxo-1,3-dihydro-isobenzofuran-5-carboxylic acid (1 g, 3.7 mmol) in thionyl chloride (25 mL) was heated at reflux for 25 min, during which time the solid dissolved. The thionyl chloride was then evaporated, and the residue was dissolved in toluene, and again evaporated. The residue was dissolved in toluene (15 mL) and was treated with a solution of ammonia in ether and a heavy precipitate formed. The mixture was stirred overnight, diluted with toluene and aqueous ammonia solution, and filtered. The residue was dried to give the title compound as a white solid (0.80 g, 80%). $^1$H NMR (d$^6$-DMSO): δ 6.81 (s, 1H), 7.25 (t, 2H), 7.40 (dd, 2H), 7.54 (d, 1H), 7.59 (bs, 1H), 8.24 (bs, 1H), 8.24 (dd, 1H), 8.42 (s, 1H).

Example 5

1-(4-Fluoro-phenyl)-3-oxo-1,3-dihydro-isobenzofuran-5-carbonitrile

A suspension of 1-(4-fluoro-phenyl)-3-oxo-1,3-dihydro-isobenzofuran-5-carboxylic acid amide (13.6 g, 0.05 mole) in thionyl chloride (40 mL) and DMF (0.25 mL) was heated at reflux for 2 hours. The thionyl chloride was then evaporated, and the residue was dissolved in hot IPA (100 mL). On cooling, crystals of the title compound were formed. Yield: 7.8 g (62%). $^1$H NMR (d$^6$-DMSO): δ 6.87 (s, 1H), 7.26 (t, 2H), 7.42 (dd, 2H), 7.58 (d, 1H), 8.18 (dd, 1H), 8.48 (s, 1H).

Example 6

5-Bromomethyl-1-(4-fluoro-phenyl)-1,3-dihydro-isobenzofuran

A suspension of 5-hydroxymethyl-1-(4-fluoro-phenyl)-1,3-dihydro-isobenzofuran (2 g, 8.2 mmol) in toluene (20 mL) was heated until the solid dissolved. Heating was then stopped. Thionyl bromide (2.2 g, 10.6 mmol) was added, and the mixture was stirred for 1 h. Silica (25 g) was added, and the mixture was filtered, and the residue was washed with a 1:1 v/v solution of ethyl acetate and heptane. The filtrate was evaporated to give the title compound as a red-orange oil (2.6 g, 90%). $^1$H NMR (d$^6$-DMSO): δ 4.72 (s, 2H), 5.11 (d, 1H), 5.28 (d, 1H), 6.17 (s, 1H), 7.04 (d, 1H), 7.17 (t, 2H), 7.33 (d, 1H), 7.38 (dd, 2H), 7.45 (s, 1H).

Example 7

5-Aminomethyl-1-(4-Fluoro-phenyl)-1,3-dihydro-isobenzofuran

A suspension of 5-bromomethyl-1-(4-fluoro-phenyl)-1,3-dihydro-isobenzofuran (1.96 g, 6.4 mmol) was stirred in liquid re-distilled ammonia (200 mL) under nitrogen/ammonia at −33° C. for 2½ days. The ammonia was allowed to evaporate, and the residue was stirred with a mixture of ethyl acetate and aqueous sulfuric acid (2 M). The aqueous phase was separated and was washed with ether. The aqueous phase was then basified to pH>9 using aqueous ammonium hydroxide solution (25% w/v), and was extracted with toluene. The toluene extracts were dried over anhydrous magnesium sulfate and evaporated to give the title compound as a yellow-orange oil (0.63 g, 40%). $^1$H NMR (d$^6$-DMSO): δ 3.72 (s, 2H), 5.09 (d, 1H), 5.25 (dd, 1H), 6.14 (s, 1H), 6.96 (d, 1H), 7.17 (t, 2H), 7.20 (d, 1H), 7.32 (s, 1H), 7.36 (dd, 2H).

Example 8

Citalopram

To a stirred solution of 5-aminomethyl-1-(3-dimethylamino-propyl)-1-(4-fluoro-phenyl)-1,3-dihydro-isobenzofuran (0.5 g, 1.5 mmol) in dichloromethane (10 mL) was added an aqueous solution of potassium bisulfate and sodium hydroxide (19 mL; 0.2 M in K$_2$S$_2$O$_8$, 3.8 mmol; 0.4 M in NaOH, 7.6 mmol), followed by an aqueous solution of nickel sulfate (1.5 mL, 40 mM, 61 μmol). The mixture was stirred vigorously for 4 days, and was then filtered through celite. The filtrate was partitioned between aqueous sulfuric acid (2 M) and toluene. The aqueous layer was separated, and the pH of the mixture was adjusted to >9 by the addition of aqueous ammonia solution (25% w/v). The solution was extracted with toluene, and this latter toluene extract was dried over magnesium sulfate and evaporated to give the free base of citalopram as a very pale yellow oil (0.35 g, 70%).

Example 9

1-(4-Fluoro-phenyl)-3-oxo-1,3-dihydro-isobenzofuran-5-carboxylic Acid

Zink (38 g, 0.58 mol) was suspended in acetic acid (400 mL). The mixture was heated to 60° C. 2,4-dicarboxy-4'-fluoro-benzophenone (21 g, 0.075 mol) was added in portions of 5 grams. After addition, the reaction mixture was heated at reflux temperature for two hours. The suspension was filtered while it was still hot. The filtrate was added to ice-water (1 kg) and the title compound was isolated by filtration. Yield 17.8 g (90%). 1H NMR (d$^6$-DMSO): δ 6.84 (s, 1H), 7.17 (t, 2H), 7.43 (dd, 2H), 7.59 (d, 1H), 8.31 (d, 1H), 8.35 (s, 1H).

What is claimed is:

1. A method for the preparation of citalopram comprising reacting a compound of Formula IV

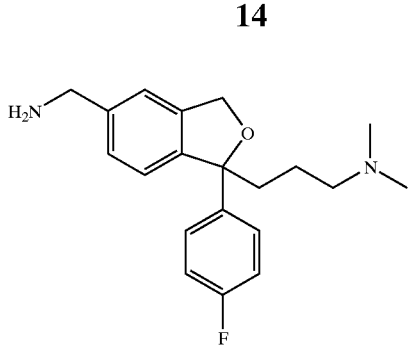

Formula IV with an oxidising agent to afford citalopram

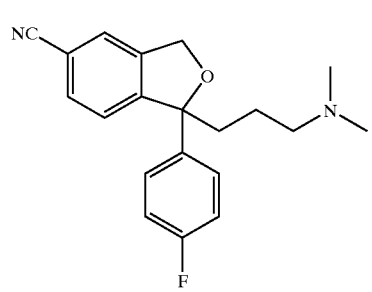

Formula I which is isolated as the base or a pharmaceutically acceptable salt thereof.

2. The method of claim 1, wherein the compound of Formula IV is prepared by activating the alcohol of Formula VIII

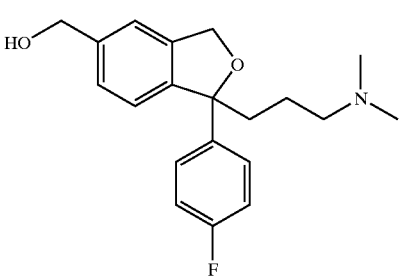

Formula VIII by a substituted sulphonate or converting the alcohol into a benzylic halide or another activated derivative followed by aminolysis to form the compound of Formula IV

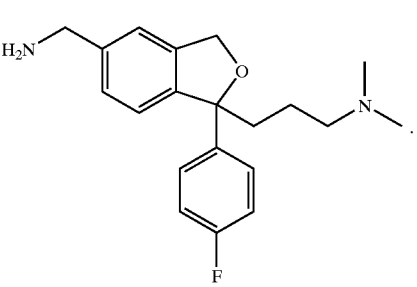

Formula IV

3. The method of claim 2, wherein the compound of Formula VIII is prepared by reacting the compound of Formula VII

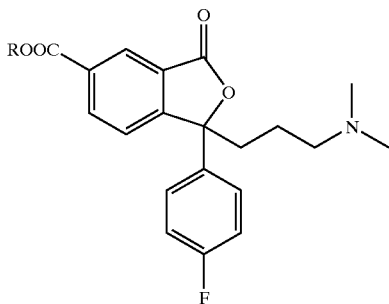

Formula VII with a reducing agent.

4. The method of claim 3, wherein the compound of Formula VII is prepared by alkylating the compound of Formula VI

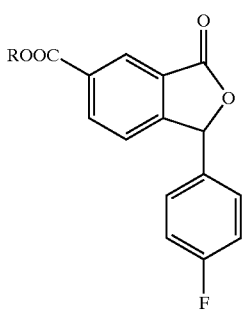

Formula VI optionally by stepwise alkylation.

5. The method of claim 4, wherein the compound of Formula VI is prepared by reacting the compound of Formula V

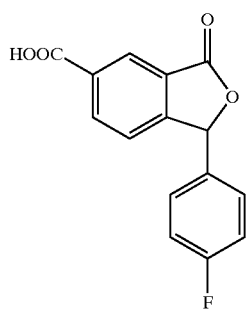

Formula V with an alcohol R—OH in the presence of a dehydrating agent.

6. The method of claim 1, wherein the compound of Formula IV is prepared by reacting the compound of Formula X

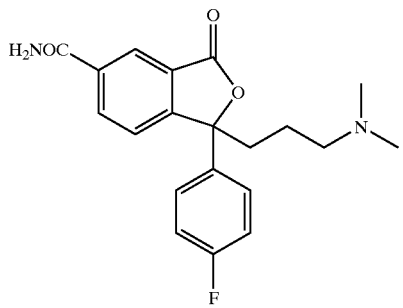

Formula X with a reducing agent followed by ring closure to form the compound of Formula IV

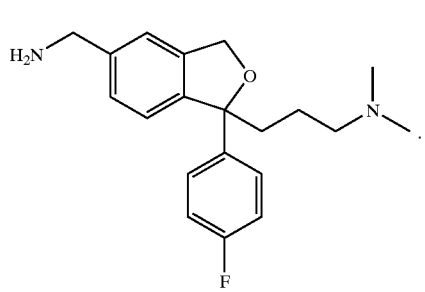

Formula IV

7. The method of claim 6, wherein the intermediate of Formula X is prepared by alkylating the compound of Formula IX

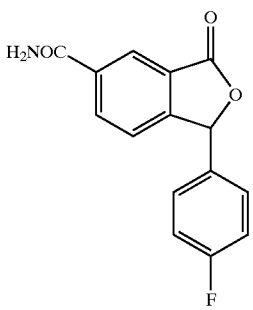

Formula IX optionally by stepwise alkylation.

8. The method of claim 7, wherein the compound of Formula IX is prepared by reacting the compound of Formula V

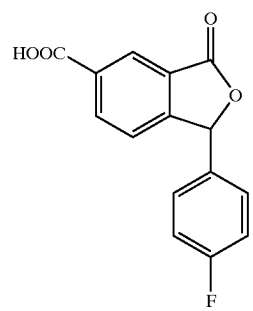

Formula V with a dehydrating agent, followed by aminolysis of the resulting activated acid derivative.

9. The method of claim 8, wherein the dehydrating agent is thionylchloride.

10. The method of claim 1, wherein the compound of Formula IV is prepared by reacting the compound of Formula XII

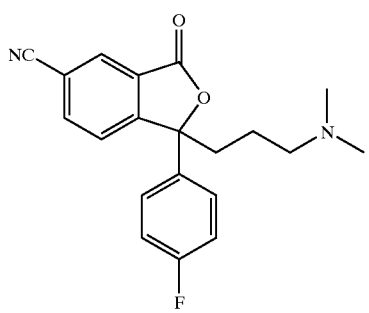

Formula XII with a reducing agent followed by ring closure to form the compound of Formula IV

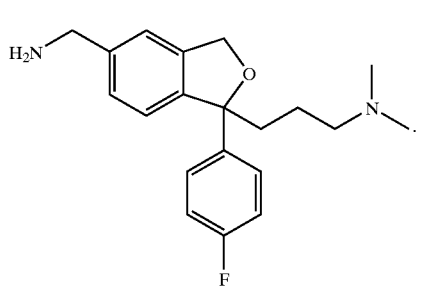

Formula IV

11. The method of claim 10, wherein the compound of Formula XII is prepared by alkylating the compound of Formula XI

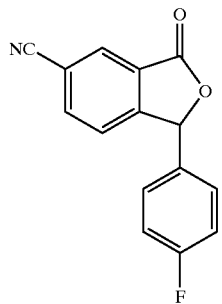

Formula XI optionally by stepwise alkylation.

12. The method of claim 11, wherein the compound of Formula XI is prepared by converting the compound of Formula V

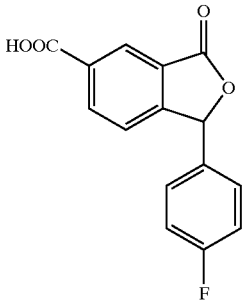

Formula V to the corresponding cyano substituted compound.

13. A compound of Formula V

Formula V

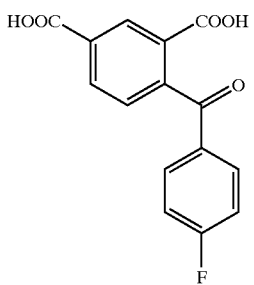

14. A method for the preparation of the compound of claim 13, comprising a ring closure reaction of a compound of Formula XIII Formula XIII with a suitable reducing agent.

15. The method of claim 14, wherein the reducing agent is Zn in acid.

16. The method of claim 15, wherein the acid is acetic acid.

17. The method of claim 1, wherein the compound of Formula IV is prepared by alkylating the compound of Formula XVII

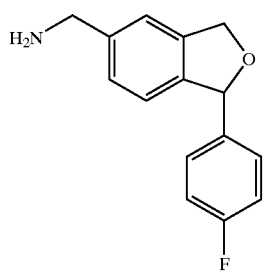

Formula XVII optionally by stepwise alkylation to form the compound of Formula IV

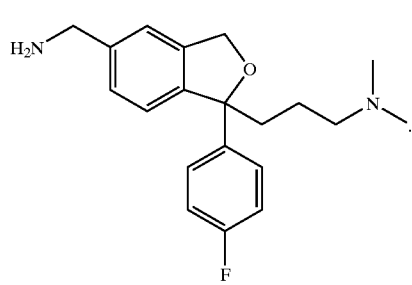

Formula IV

18. The method of claim 17, wherein the compound of Formula XVII is prepared by aminolysis of the compound of Formula XVI

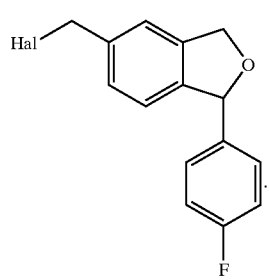

Formula XVI

19. The method of claim 18, wherein the compound of Formula XVI is prepared by activating the alcohol of Formula XV

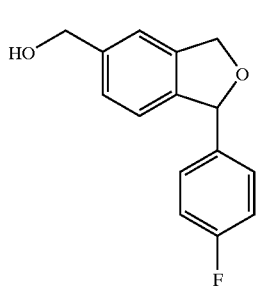

Formula XV by a substituted sulphonate or converting the alcohol into a benzylic halide or another activated derivative.

20. The method of claim 19, wherein the intermediate of Formula XV is prepared by reacting the ketone of Formula XIII

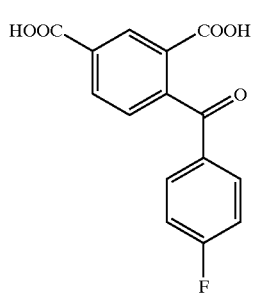

Formula XIII with a reducing agent followed by ring closure to form the compound of Formula XV.

21. An antidepressant pharmaceutical composition comprising citalopram manufactured by the method of claim 1.

* * * * *